(12) United States Patent
Cohen et al.

(10) Patent No.: US 7,524,670 B2
(45) Date of Patent: Apr. 28, 2009

(54) PROTOCOL AND APPARATUS FOR DETERMINING HEPARIN-INDUCED THROMBOCYTOPENIA

(75) Inventors: Eli Cohen, Skokie, IL (US); Roslyn Cohen, Chicago, IL (US); Roger C. Carroll, Knoxville, TN (US)

(73) Assignee: Haemoscope Corporation, Niles, IL (US)

( * ) Notice: Subject to any disclaimer, the term of this patent is extended or adjusted under 35 U.S.C. 154(b) by 411 days.

(21) Appl. No.: 10/634,553

(22) Filed: Aug. 5, 2003

(65) Prior Publication Data

US 2005/0032142 A1 Feb. 10, 2005

(51) Int. Cl.
*C12M 1/34* (2006.01)
(52) U.S. Cl. .................................. 435/287.1
(58) Field of Classification Search ........................ None
See application file for complete search history.

(56) References Cited

U.S. PATENT DOCUMENTS

| | | | |
|---|---|---|---|
| 3,714,815 A | 2/1973 | Hartert | |
| 4,148,216 A | 4/1979 | Do et al. | |
| 4,193,293 A | 3/1980 | Cavallari | |
| 4,312,217 A | 1/1982 | Hartert | |
| 4,317,363 A | 3/1982 | Shen | |
| 4,328,701 A | 5/1982 | Mau-Tung et al. | |
| 4,695,956 A | 9/1987 | LeVeen et al. | |
| 5,167,145 A | 12/1992 | Butler et al. | |
| 5,223,227 A | 6/1993 | Zuckerman | |
| 5,466,582 A | 11/1995 | Amiral | |
| 5,523,238 A | 6/1996 | Varon et al. | |
| 5,777,215 A | 7/1998 | Calatzis et al. | |
| 5,854,423 A | 12/1998 | Venegas | |
| 5,939,276 A | 8/1999 | Tomer | |
| 5,972,712 A | 10/1999 | Baugh et al. | |
| 5,972,717 A | 10/1999 | Aster et al. | |
| 6,027,904 A | 2/2000 | Devine et al. | |
| 6,060,323 A | 5/2000 | Jina | |
| 6,225,126 B1 | 5/2001 | Cohen et al. | |
| 6,537,819 B2 | 3/2003 | Cohen et al. | |
| 6,613,573 B1 | 9/2003 | Cohen | |
| 2002/0178126 A1 | 11/2002 | Beck et al. | |
| 2002/0197697 A1 | 12/2002 | Abdelouahed et al. | |
| 2002/0198740 A1 | 12/2002 | Roman et al. | |

FOREIGN PATENT DOCUMENTS

| | | |
|---|---|---|
| DE | 37 38 901 A1 | 5/1989 |
| EP | 0 018 905 A1 | 11/1980 |
| EP | 0 404 456 A2 | 12/1990 |
| EP | 0 525 273 A1 | 2/1991 |
| EP | 1 226 781 A2 | 7/2002 |
| EP | 1 371 98 A1 | 12/2003 |
| FR | 2 389 137 | 11/1978 |
| GB | 2 004 376 | 3/1979 |
| WO | WO-97/41432 A1 | 11/1997 |
| WO | WO-00/49402 A1 | 8/2000 |
| WO | WO-01/04159 A1 | 1/2001 |
| WO | WO-01/50950 A2 | 7/2001 |
| WO | WO-01/96879 A2 | 12/2001 |
| WO | WO-02/054088 A2 | 7/2002 |
| WO | WO-2004/092742 A1 | 10/2004 |

OTHER PUBLICATIONS

Yamamoto et al. Am J Kidney Diseases 1996;28(1):82-85.*
Iwaki et al. "Suppression of Platelet Aggregation by *Bordetella pertussis* Adenylate Cyclase Toxin", Infection and Immunity, 1999, 67(6):2763-2768.*
Shore-Lesserson et al., Thromboelastography-Guided Transfusion Algorithm Reduces Transfusions in Complex Cardiac Surgery, Anesthesia and Analgesis (abstract), Feb. 1999, 1 page.
Frenette et al., Effectiveness of Conjugated Estrogen in Orthotopic Liver Transplantation, Southern Medical Journal, vol. 91, Apr. 1998, pp. 365-368.
Nguyen et al., A Web-Based Teaching Program for Laboratory Diagnosis of Coagulation Disorders, Arch. Pathol. Lab. Med., vol. 124, Apr. 2000, pp. 588-593.
International Search Report for Application No. PCT/US03/30710 dated Apr. 21, 2004.
Edwards et al., "Successful Use of Argatroban as a Heperin Substitute During Cardiopulmonary Bypass: Heparin-Induced Thrombocytopenia in a High-Risk Cardiac Surgical Patient," The Annals of Thoracic Surgery, vol. 75, May 2003, pp. 1622-1624.
Ammar et al., "In Vitro Effects of the Platelet Glycoprotein IIb/IIIa Receptor Antagonist c7E3 Fab on the Activated Clotting Time," Circulation, vol. 95, No. 3, Feb. 4, 1997, pp. 614-617.
Koster et al., "Recombinant Hirudin as an Alternative for Anticoagulation During Cardiopulmonary Bypass in Patients with Heparin-Induced Thrombocytopenia Type II: A 1-Year Experience in 57 Patients," Journal of Cardiothoracic and Vascular Anethesia, vol. 14, No. 3, Jun. 2000, pp. 243-248.
Muhl et al., "Therapy and Monitoring of Heparin-Induced Thrombocytopenia Type II in Critically ill Patients During Continuous Venovenous Hemodiafiltration: Comparsion of aPTT and Ecarin Clotting Time for Monitoring of r-Hirudin Therapy," Journal of Intensive Care Medicine, vol. 17, No. 1, Jan./Feb. 2002, pp. 34-40.
International Search Report for Application No. PCT/US04/025250 dated Jan. 10, 2005.
Mahaffey, "Anticoagulation for Acute Coronary Syndromes and Percutaneous Coronary Intervention in Patients with Heparin-inducted Thrombocytopenia," Current Cardiology Reports, vol. 3, pp. 362-370.

(Continued)

*Primary Examiner*—Jon P Weber
*Assistant Examiner*—Bin Shen
(74) *Attorney, Agent, or Firm*—Marshall, Gerstein & Borun LLP

(57) ABSTRACT

A hemostasis analyzer, such as the Thrombelastograph® (TEG®) hemostasis analyzer is utilized to measure continuously in real time, the hemostasis process from the initial fibrin formation, through platelet-fibrin interaction and lysis to generate blood hemostasis parameters. The measured blood hemostasis parameters permit determination of heparin-induced thrombocytopenia II complex (HiT II).

21 Claims, 4 Drawing Sheets

OTHER PUBLICATIONS

Gaetano et al., *Effect of Platelets on Clot Structuration. A Thromebelastographic Study*, Thrombosis Research, vol. 3, 1973, pp. 425-435.

Greilich et al., *A Modified Thromboelastographic Method for Monitoring c7E3 Fab in Heparinized Patients*, Anesth Analg., vol. 84, pp. 31-38.

Khurana et al., *Monitoring Platelet Glycoprotein IIb/IIIa-fibrin Interaction With Tissue Factor-Activated Thromboelastography*, J Lab Clin Med, 1997, pp. 401-411.

Timmis et al., *Advances in Antiplatelet Therapy in Coronary Artery Disease: Importance of the Platelet GPIIb/IIIa Receptor*, Journal of Interventional Cardiology, vol. 10, No. 5, 1997, pp. 327-333.

*Ultegra Rapid Platelet Function Assay (RPFA) Bedside Monitoring*, Cath-Lab Digest, vol. 7, No. 6, 1999, pp. 1-3.

Dambisya et al., *Effects of the Platelet-Activating Factor Receptor Antagonist WEB 2086 on Whole Blood Coagulation and Fibrinolysis in a Thromboelastography Assay*, Blood Coagulation and Fibrinolysis, vol. 6, 1995, pp. 733-737.

Orbitometer—The consequent development of the precusory Thrombo-Elastography (Hartert 1947) and of resonance-Thrombography (Hartert 1977), Heinrich Amelung GmbH, 6 pages.

roTEG Coagulation Analyzer, 1997 Dynabyte Medical, 2 pages.

Pravinkumar et al., *HIT/HITT and alternative anticoagulation: current concepts*, British Journal of Anaesthesia, pp. 676-685, 2003.

\* cited by examiner

PROTOCOL AND APPARATUS FOR DETERMINING HEPARIN-INDUCED THROMBOCYTOPENIA

CROSS-REFERENCE TO RELATED APPLICATIONS

This application is related to the following commonly owned United States patents and patent applications: U.S. patent application Ser. No. 09/591,371 filed Jun. 9, 2000 entitled Method and Apparatus for Monitoring Anti-Platelet Agents; U.S. patent application Ser. No. 10/384,345 filed Mar. 2, 2003 entitled Protocol for Monitoring Platelet Inhibition; U.S. patent application Ser. No. 10/409,479 filed Apr. 8, 2003 entitled Method and Apparatus for Monitoring Hemostasis in Connection with Artificial Surface Devices and U.S. Pat. No. 6,225,236 entitled Method and Apparatus for Measuring Hemostasis, the disclosures of which are hereby expressly incorporated herein by reference.

TECHNICAL FIELD

The present invention relates to a protocol and apparatus for determining heparin-induced thrombocytopenia (HiT).

BACKGROUND

Blood is the circulating tissue of an organism that carries oxygen and nutritive materials to the tissues and removes carbon dioxide and various metabolic products for excretion. Whole blood consists of pale yellow or gray yellow fluid, plasma, in which are suspended red blood cells, white blood cells, platelets, and hemostatic factors.

An accurate measurement of the ability of a patient's blood to coagulate and lyse, i.e., hemostasis, in a timely and effective fashion is crucial to certain surgical and medical procedures. Accelerated (rapid) and accurate detection of abnormal hemostasis is also of particular importance with respect to appropriate treatment to be given to patients suffering from coagulopathies and to whom it may be necessary to administer anticoagulants, antifibrinolytic agents, thrombolytic agents, anti-platelet agents, or blood components in a quantity which must clearly be determined after taking into account the abnormal components or "factors" of the patient's blood and prior hemostasis treatment that may be contributing to the present hemostasis disorder.

Hemostasis is a dynamic, extremely complex process involving many interacting factors, which include coagulation and fibrinolytic proteins, activators, inhibitors and cellular elements, such as platelet cytoskeleton, platelet cytoplasmic granules and platelet cell surfaces. As a result, during activation, no factor remains static or works in isolation. The beginning of the coagulation process is platelet aggregation (FIG. 1a) and the initial phase of the enzymatic reaction. The end result of the coagulation process is a three dimensional network of polymerized fibrin(ogen) fibers which together with platelet glycoprotein IIb/IIIa (GPIIb/IIIa) receptor bonding forms the final clot (FIG. 1b). A unique property of this network structure is that it behaves as a rigid elastic solid, capable of resisting deforming shear stress of the circulating blood. The strength of the final clot to resist deforming shear stress is determined by the structure and density of the fibrin fiber network and by the forces exerted by the participating platelets.

Thus, the clot that develops and adheres to the damaged vascular system as a result of activated coagulation and resists the deforming shear stress of the circulating blood is, in essence, a mechanical device, formed to provide a "temporary stopper," which resists the shear force of circulating blood during vascular recovery. The kinetics, strength, and stability of the clot, that is, its physical property to resist the deforming shear force of the circulating blood, determine its capacity to do the work of hemostasis, which is to stop hemorrhage without permitting inappropriate thrombosis. This is exactly what the Thrombelastograph® (TEG®) hemostasis analysis system, described below, is designed to do, which is to measure the time it takes for initial fibrin formation, the time it takes for the clot to reach its maximum strength, the actual maximum strength, and the clot's stability.

Blood hemostasis analyzer instruments have been known since Professor Helmut Hartert developed such a device in Germany in the 1940's. One type of blood hemostasis analyzer is described in commonly assigned U.S. Pat. Nos. 5,223,227 and 6,225,126, the disclosures of which are hereby expressly incorporated herein by reference. This instrument, the TEG® hemostasis analysis system, monitors the elastic properties of blood as it is induced to clot under a low shear environment resembling sluggish venous blood flow. The patterns of changes in shear elasticity of the developing clot enable the determination of the kinetics of clot formation, as well as the strength and stability of the formed clot; in short, the mechanical properties of the developing clot. As described above, the kinetics, strength and stability of the clot provides information about the ability of the clot to perform "mechanical work," i.e., resisting the deforming shear stress of the circulating blood; in essence, the clot is the elementary machine of hemostasis, and the TEGS® hemostasis analysis system measures the ability of the clot to perform mechanical work throughout its structural development. The TEG® hemostasis analysis system measures continuously all phases of patient hemostasis as a net product of whole blood components in a non isolated, or static fashion from the time of test initiation until initial fibrin formation, through clot rate strengthening and ultimately clot strength through fibrin platelet bonding via platelet GPIIb/IIIa receptors and clot lysis.

Heparin is one of the most widely prescribed anticoagulant drugs and has been very successful. However, heparin also has some potential adverse affects. As with any anti-coagulant, there is a risk of bleeding. Heparin has also been associated with an increased risk of osteoporosis, cutaneous reactions, and a condition referred to as heparin-induced thrombocytopenia (HiT).

HiT has been observed to occur in two forms. The first, type-I or non-immune HiT (HiT I), is commonly seen in patients receiving full dose intravenous unfractionated heparin. The fall in platelet count resulting from the introduction of heparin in HiT I is transient, is not associated with any adverse effects and is self-limiting insofar as it will resolve even if heparin therapy is continued. It is largely the result of heparin's binding directly to platelets.

Type-II, or immune-mediate HiT (HiT II), is the result of an antigen-antibody reaction. In HiT II, heparin-induced antibodies may form due to frequent exposure of patient blood to heparin. There is a high binding affinity between heparin and platelet factor four (PF4). Upon binding to the heparin molecule, PF4 exposes antigenic epitopes, which trigger the immune system and the production of immunoglobin G (IGH).

The IGH antibody binds to the antigen and to the platelets via the Fc fragment. Occupation of adjacent Fc receptors on the platelet membrane causes intense platelet activation resulting into lower platelet number (thrombocytopenia) and thrombosis in the form of white clot thrombi, leading to high risk of morbidity and mortality.

The Heparin-PF4-IGH referred to here as the HiT II complex.

There are two main classes of assays for laboratory diagnosis of HiT II: activation (functional) assays and antigen assays. The functional assays include the platelet aggregation assay and the serotonin release assay. The platelet aggregation assay is performed in the laboratory with a specificity>90%. The disadvantage is low sensitivity, <35%, i.e., a relatively high probability of false negative.

The serotonin release assay measures the release of serotonin from platelet aggregates. It relies on the aggregation of the platelets from the patient in the presence of heparin. This assay has high sensitivity and specificity. The disadvantage is that the assay is technically demanding and involves the use of radioactive materials. Of the various available functional assays available, platelet aggregation using washed platelets and platelet serotonin release are considered the most accurate.

The other class of assays is the antigen assays. The heparin-PF4 enzyme-linked immunosorbent assay (ELISA) relies on the specificity of the HiT IGH antibodies for the heparin-PF4 complex. This assay is 10 times more sensitive than the serotonin release assay for detecting heparin-induced antibodies. However, the heparin-PF4 ELISA is expensive and time consuming. The assay also responds to clinically insignificant antibodies more often than functional assays, and hence has a lower specificity, i.e., a relatively high probability of false positive.

Thus, most of the available laboratory tests for the diagnosis of HiT II are expensive, time-consuming, frequently contradictory and vary in sensitivity and specificity.

Because of the mortality and morbidity risk associated with treating a HiT II patient with additional heparin or platelets, the clinician must often resort, unnecessarily, to recommending another anticoagulant agent to be used instead of heparin when HiT II is suspected. However, other agents are more expensive and it is difficult or impossible to measure the extent of anticoagulation for proper dosing of the patient to prevent ischemic events. These anticoagulants also lack the agents necessary to reverse their anticoagulant effect, which may result with uncontrollable post-surgical hemorrhage.

Thus, there is a need for a method and apparatus for determining heparin-induced thrombocytopenia.

DETAILED DESCRIPTION

In accordance with the preferred embodiments of the invention, a hemostasis analyzer, such as the Thrombelastograph® (TEG®) hemostasis analyzer available from Haemoscope Corp., Niles, Ill., is utilized to measure continuously in real time, the hemostasis process from the initial fibrin formation, through platelet-fibrin GPIIb/IIIa bonding and lysis. While specific protocols and apparatus are discussed for determining whether a patient has heparin-induced thrombocytopenia (HiT), it will be appreciated that the invention has application in connection with other diagnostic techniques whether related to HiT or otherwise.

In accordance with the embodiments of the invention described herein, utilization of the hemostasis analyzer in accordance with the inventive protocol permits confirmation of the onset of HiT II using either patient whole blood or using normal donor platelet rich plasma (PRP) and HiT II suspect patient plasma mixture. The whole blood testing protocol provides a point-of-care testing capability, while the PRP-patient plasma mixture protocol provides a laboratory testing capability. Either protocol relies on measurement of one or more physical characteristics of the blood clot as measured by the hemostasis analyzer. These characteristics include clot strength or elasticity, time to initial clot formation, rate of clot formation or strengthening, rate of clot lysis, and the like. Several samples prepared according to the particular protocol being employed may be tested in one or more testing stations of a hemostasis analyzer.

Figure 1A:
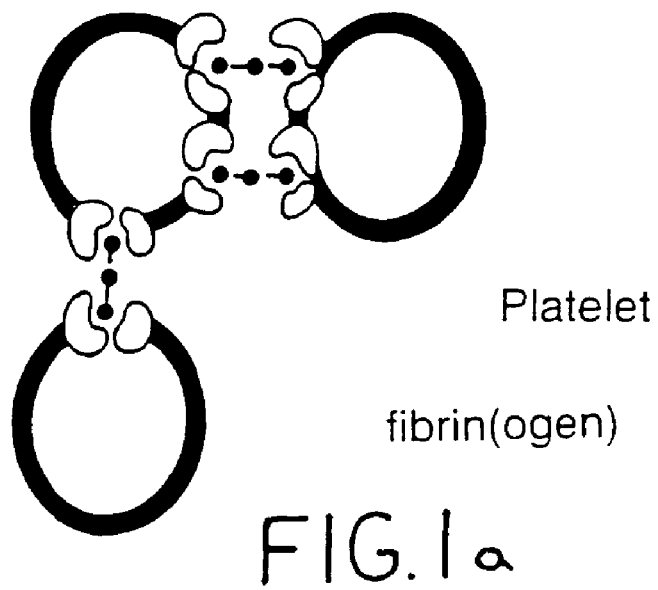
FIG. 1a is graphic illustration representing the mechanism of platelet aggregation.
Figure 1B:
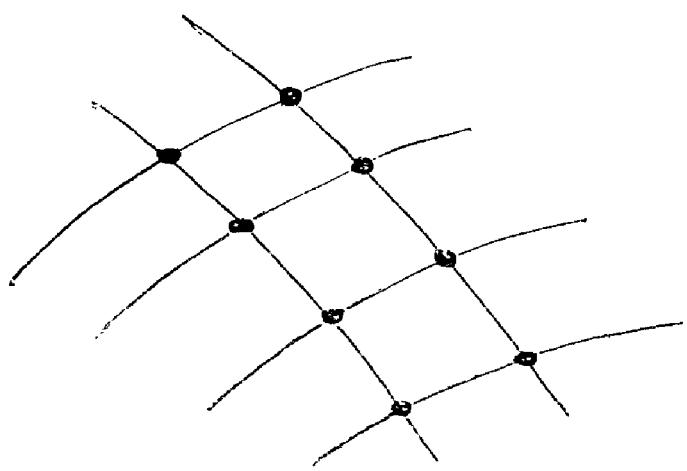
FIG. 1b is graphic illustration representing a fibrin/platelet network.
Figure 2:
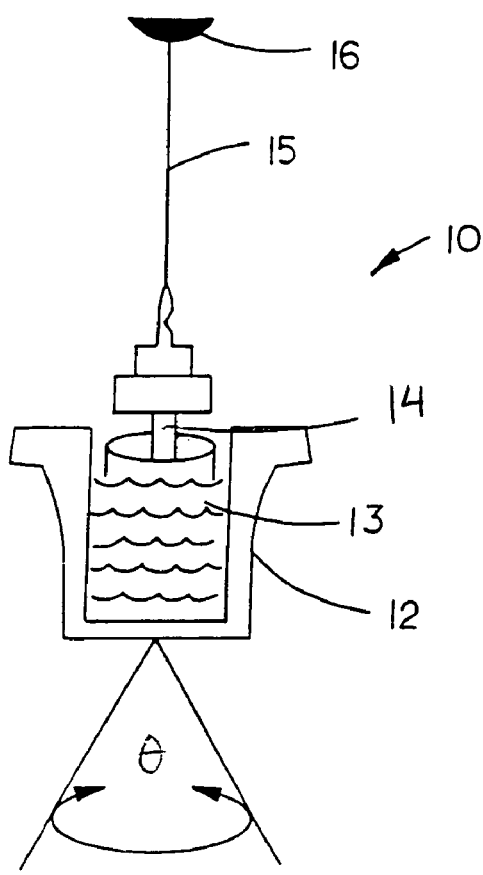
FIG. 2 is a schematic diagram of a hemostasis analyzer in accordance with a preferred embodiment of the invention.

A hemostasis analyzer 10, such as the Thrombelastograph® (TEG®) hemostasis analyzer referenced above, may be used to measure the physical properties of a clot formed during testing of a patient blood sample. The term patient blood sample is used throughout and interchangeably to refer to a patient whole blood sample, a PRP-patient plasma mixture, or other appropriate patient blood samples. An exemplary hemostasis analyzer 10 is described in detail in the aforementioned U.S. Pat. No. 6,225,126, and a complete discussion is not repeated here. With reference to FIG. 2, to assist in the understanding of the invention, however, a brief description of the hemostasis analyzer 10 is provided. The hemostasis analyzer uses a special stationary cylindrical cup 12 that holds a blood sample 13. The cup 12 is coupled to a drive mechanism that causes the cup to oscillate through an angle θ, preferably about 4° 45'. Each rotation cycle lasts 10 seconds. A pin 14 is suspended in the blood sample 13 by a torsion wire 15, and the pin 14 is monitored for motion. The torque of the rotating cup 12 is transmitted to the immersed pin 14 only after fibrin-platelet bonding has linked the cup 12 and pin 14 together. The strength of these fibrin-platelet bonds affects the magnitude of the pin motion, such that strong clots move the pin 14 directly in phase with the cup motion. Thus, the magnitude of the output is directly related to the strength of the formed clot. As the clot retracts or lyses, these bonds are broken and the transfer of cup motion is diminished.

The rotational movement of the pin 14 is converted by a transducer 16 to an electrical signal, which can be monitored by a computer (not shown in FIG. 2) including a processor and a control program.

The computer is operable on the electrical signal to create a hemostasis profile corresponding to the measured clotting process. Additionally, the computer may include a visual display or be coupled to a printer to provide a visual representation of the hemostasis profile. Such a configuration of the computer is well within the capabilities of one having ordinary skill in the art.

Figure 3:
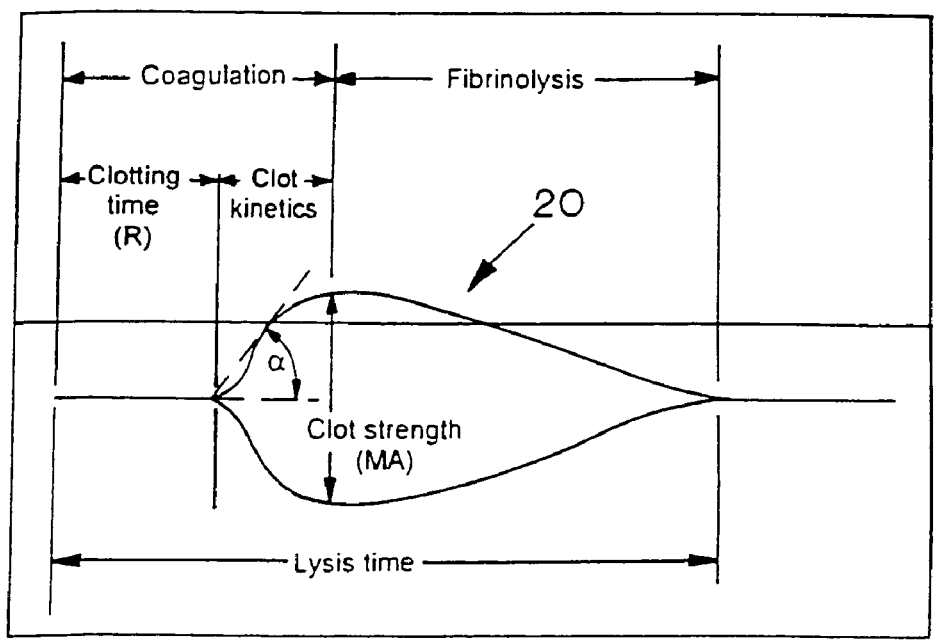
FIG. 3 is a plot illustrating a hemostasis profile generated by the hemostasis analyzer shown in FIG. 2.

As will also be described, based upon an assessment of the hemostasis profile, the computer, through its control program, may be adapted to provide treatment recommendations. As shown in FIG. 3, the resulting hemostasis profile 20 is a measure of the time it takes for the first fibrin strand to be formed, the kinetics of clot formation, the strength of the clot (measured in millimeters (mm) and converted to shear elasticity units of dyn/cm$^2$) and dissolution of clot. Table I, below, provides definitions for several of these measured parameters.

TABLE I

| | |
|---|---|
| R | R time is the period of time of latency from the time that the blood was placed in the TEG ® analyzer until the initial fibrin formation. |
| α | a measures the rapidity of fibrin build-up and cross-linking (clot strengthening) |
| MA | MA, or Maximum Amplitude in mm, is a direct function of the maximum dynamic properties of fibrin and platelet bonding via GPIIb/IIIa and represents the ultimate strength of the fibrin clot. |
| LY30 | LY30 measures the rate of amplitude reduction 30 minutes after MA and represents clot retraction, or lysis. |

Clinically, these measurements provide a vehicle for monitoring anti-coagulation therapy (e.g. heparin or warfarin), thrombolytic therapy (e.g. tPA, streptokinase, urokinase), effect of antifibrinolytics (e.g. ϵ-amino-caproic acid (Amicar®), trasylol (aprotinin), tranexamic acid (TX)), effect of anti-platelet agents (e.g. abciximab (ReoPro®), eptifibatide (Integrilin®), tirofiban (Aggrastat®), blood component transfusion therapy, thrombotic risk assessment in cancer and infection, high risk surgery and other conditions which could possibly lead to excessive clotting (hypercoagulable conditions) or excessive bleeding (hypocoagulable conditions). In accordance with embodiments of the invention then, the hemostasis analyzer 10 is useful in testing the clinical efficacy of drug therapy to stop fibrinolysis, or the efficacy of thrombolytic drugs to monitor thrombolysis, efficacy of anti-platelet agents to monitor platelet inhibition, ischemic or bleeding complications.

Quantitatively, the hemostasis analyzer 10 and associated computer plot the strength of the clot against time, where the onset of clot formation, the reaction time (R), is noted (FIG. 3). This plot also indicates the maximum clot strength (or rigidity), MA, of a blood sample. MA is an overall estimate of platelet-fibrin GPIIb/IIIa bonding, which is used, for example, to guide post-operative blood platelet or fibrinogen replacement therapy. Between platelets and fibrin alone, an abnormally low MA implies that there is an abnormality in blood platelets (i.e., a quantitative or functional defect) and/or an abnormality in fibrinogen content in the blood. However, by keeping fibrinogen level and platelet number constant, any change in MA would reflect changes in platelet function. Therefore, an increased MA value reflects higher platelet function while a lower MA reflects platelet function as it diminishes until it reaches the limit of zero platelet activity, at which point only fibrin contributes to the MA. However in the absence of any other platelet activator/agonist, the presence of HiT II complex activates platelets increasing the MA value beyond that of fibrin. Therefore, in accordance with the above, in order to properly monitor HiT II, the following procedure may be followed:

1. The TEG-5000, as it is commonly used, measures platelet function (MA) that is stimulated by thrombin, the most potent platelet activator that directly activates the GPIIb/IIIa receptor site. To sensitize MA to a small activation of platelet function, platelet function such as HiT II complex, thrombin should be inhibited. Therefore, when running blood samples in the TEG hemostasis analyzer, formation of thrombin is inhibited with direct thrombin inhibitor, for example, PPACK (phenylalanyl-prolyl-arginine chloromethyl ketone).

2. Unfortunately, thrombin is also involved in activating the fibrinogen to fibrin conversion. Having inhibited thrombin formation in Step 1, it is necessary to use another enzyme to activate fibrinogen. Reptilase (Batroxabin), whose sole function is to activate fibrinogen to fibrin, is a suitable enzyme. The clot is now stimulated by reptilase (fibrinogen activator) and weaker platelet agonist such as HiT II complex. The strength of the clot is measured by MA, as described above.

3. The clot that is formed by a fibrinogen activator like reptilase and platelet activation by HiT II complex is typically weaker than one developed by thrombin. Therefore, activated Factor XIII (Factor XIIIa) may be added. Factor XIIIa causes a modification of the fibrin network from hydrogen bonding to stronger covalent bonding referred to as fibrin cross linking, which further enhances fibrin clot strength.

Based on the above, the following protocol may be implemented.

Figure 4:
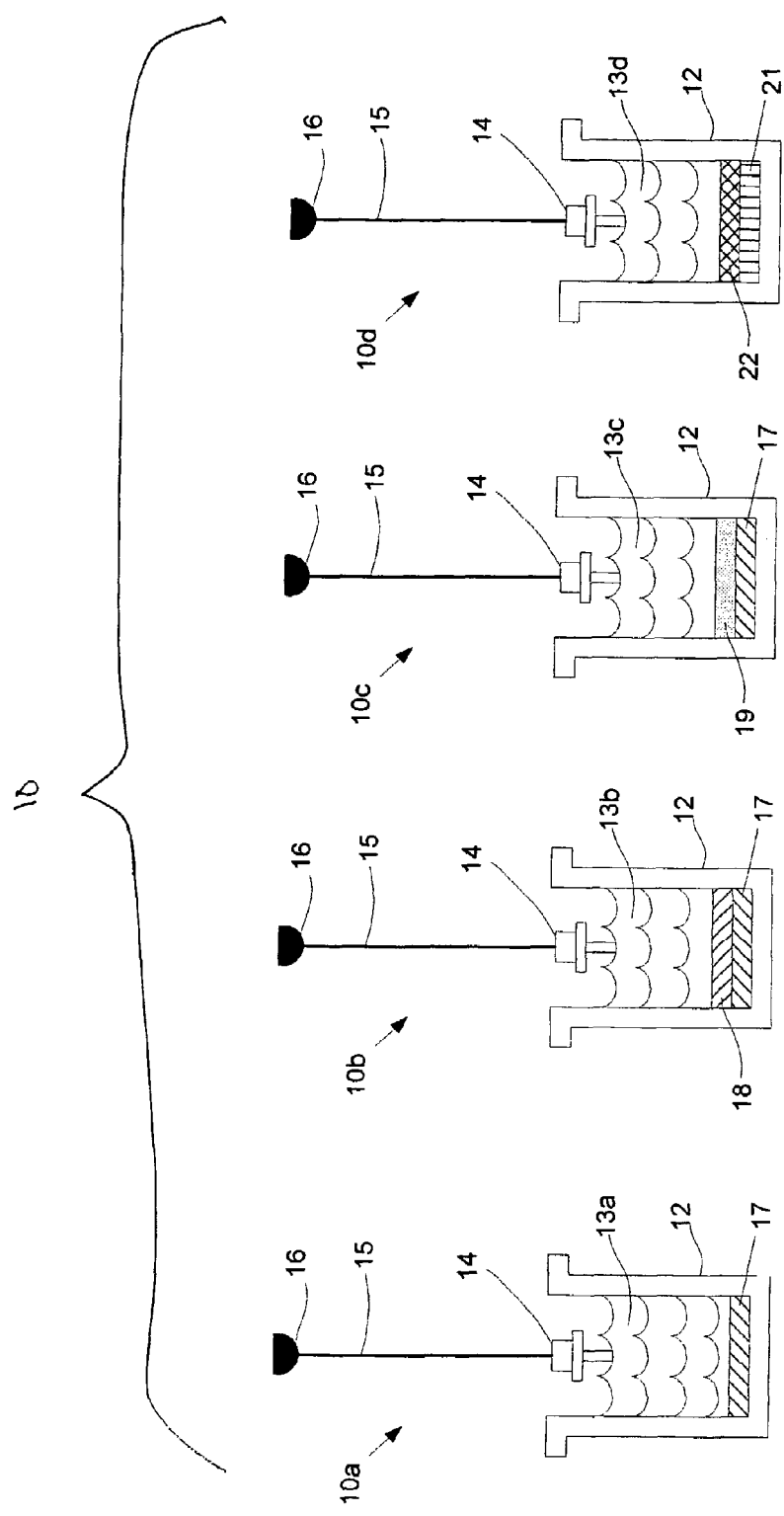
FIG. 4 is a schematic diagram of a hemostasis analyzer in accordance with an embodiment of the invention.

Referring to FIGS. 4 and 5, a protocol is described for determining HiT II using a hemostasis analyzer. FIG. 4 illustrates four testing stations 10a, 10b, 10c and 10d of a hemostasis analyzer 10'. Each station may be substantially similar to the station 10 described in connection with FIG. 2, or may be of another configuration. The stations may also be part of separate testing apparatus, for example, there may be-four signal station devices, two dual station devices, one four station devices, etc. Each station is configured to testing a corresponding blood sample and to provide a blood sample characteristic. For example, each station may be configured to provide the parameters R, α, MA and LY 30 for each blood sample. A first blood sample 13a, may be a baseline sample. The second and third samples 13b and 13c may have varying amounts of heparin added. The fourth sample 13d may be prepared to substantially completely suppress platelet activation. For example, this may be achieved by including in the sample a sufficiently large quantity of heparin. Each of the samples is tested and the MA reported for each sample. The MA of the first sample 13a represents the fibrin contribution to clot strength absent substantial platelet activation, i.e., $MA_{FIB}$. Given the near complete suppression of platelet activation in the sample 13d, the MA of this sample should be very nearly the same as $MA_{FIB}$. In the presence of HiT antibodies, there will be some platelet-platelet aggregation resulting in a greater MA than that of fibrin contribution alone, i.e., $MA_{FIB}$. Thus, if the MA of the samples 13b and 13c is measurably greater than $MA_{FIB}$, for example approximately 1.5 to 3 times greater, HiT II is indicated.

From the foregoing the following protocols may be defined.

EXAMPLE 1

Assaying HiT II Using Normal Donor Platelet Rich Plasma Mixed with HiT II Patient Citrated Plasma Normal donor whole blood is drawn and transferred to a plastic centrifuge tube with 5-15 ul of PPACK for each 1 ml of blood. Normal donors should have a platelet count>150,000/ul and not be taking NSAIDS or other platelet inhibitors. For a typical test, 12 ml of blood is drawn and added to a tube containing approximately 180 ul of PPACK. The tube is capped and mixed by inverting several times, e.g., 3 times. The sample is centrifuged 100 g for 20 minutes (for standard IEC table top centrifuge this is 800 RPM) to separate platelet rich plasma (PRP) from other blood cells. This procedure should result in sufficient PRP for 3-4 test mixtures, and the excess PRP may be stored at −35 to −70 degrees C. until assay.

A PRP-patient plasma mixture is prepared. Patient plasma is isolated by standard procedures from citrated whole blood stored at −30 to −70 degrees C. The normal PRP is added to thawed, room temperature test patient plasma in the ratio of approximately 2:1, e.g., approximately 1.6-1.2 ml PRP is added to approximately 0.8-0.6 ml test patient plasma, and mixed well. This procedure is only for citrated plasma, not for sera or plasma collected into other anticoagulants, nor for HiT patient whole blood.

Four sample vessels are readied for testing. To the first sample vessel 5 ul saline is added. To the second sample vessel 5 ul of 1 U/ml heparin is added. To the third sample vessel 5 ul of 3 U/ml heparin is added. To the fourth sample vessel 5 ul of 30 U/ml heparin is added. The heparin may be provided in pre-packaged tubes/vials of the appropriate concentrations. For example, HiT1, HiT3 and HiT30 vials may be provided containing various amounts of heparin.

To each sample vessel, 350 µl PRP-patient plasma mixture is added and mixed, e.g., 3 times mixing with pipet. If done in the above sequence, a single pipet may be used. The samples, except for the first vessel, are incubated at 37 degrees C. for at least 10 minutes. If a TEG® hemostasis analyzer is being used, the cups may be slide to the testing position to get slow mixing and to avoid evaporation. Other techniques for mixing and for avoiding evaporation may be employed, particularly if a non-TEG® hemostasis analyzer is not employed.

To assay, to each sample vessel approximately 10 ul of an activator is added and immediately mixed, e.g., 3 times mixing with another pipet of 350 µl PRP-patient plasma mixture. The sample vessel is then rapidly moved to the testing position and the test initiated. The test should be started within 30 seconds of adding the activator. The activator may be a combination of Reptilase® and FXIIIa or Reptilase®, FXIIIa and Epinephrine. Once the µl PRP-patient plasma mixture and 10 ul of activator are added to each vessel, the first vessel will contain no added heparin, the second vessel will contain 1 U/ml heparin, the third vessel will contain 3 U/ml heparin and the fourth vessel will contain 30 U/ml heparin.

The test is continued until stable maximum amplitude is obtained. The expected positive result for HiT II is that either the second or third sample, 1 U/ml heparin or 3 U/ml heparin, respectively, will give an MA response greater than the sample 1 MA. For example, the MA of the second or third sample should be approximately 1.5-3 times greater than the MA for sample 1. In one embodiment the expected MA2 and/or MA3 is >10 mm, using the TEG® hemostasis analyzer parameter MA, and is 2 times greater than MA1 or MA4. This may be expressed as:

$$MA2 \text{ and/or } MA3\ 2X > MA1 \approx MA4$$

which is a positive indication for HiT II. The MA of sample 4, 30 U/ml heparin, should appear substantially equal to the MA of sample 1 due to the substantially complete platelet suppression of the overwhelming amount of heparin added to the sample.

EXAMPLE 2

Assaying HiT II Using Patient Whole Blood

A sample 3 ml of suspect HiT II patient whole blood is drawn into a plastic tube with approximately 5 ul of 5 mg/ml PPACK for each 1 ml of blood. The patient should have a platelet count >50,000/ul. In addition, the patient should not be on GPIIb/IIIa inhibitor drugs such as ReoPro®, Integrilin® and Aggrestat; or other drugs that mask platelet activation by the HiT II antibody complex.

For a typical test, 6 ml of patient blood is drawn into a plastic tube with 30 ul PPACK and is mixed. This provides sufficient sample blood for the assay and will provide enough left over to isolate plasma for a confirming test with normal donor blood as described above in Example 1, especially if the patient has a platelet count <50,000/µl.

Four sample vessels are readied for testing. To the first sample vessel 5 ul saline is added. To the second sample vessel 5 ul of 1 U/ml heparin is added. To the third sample vessel 5 ul of 3 U/ml heparin is added. To the fourth sample vessel 5 ul of 30 U/ml heparin is added. The heparin may be provided in pre-packaged tubes/vials of the appropriate concentrations. For example, HiT1, HiT3 and HiT30 vials may be provided containing various amounts of heparin.

To each sample vessel 350 ul of the anticoagulated whole blood is added and mixed, e.g., three times mixing with pipet. If done in the sequence described above, a single pipet may be used for the additions and mixing. The samples, except for the first vessel, are incubated at 37 degrees C. for at least 10 minutes. If a TEG® hemostasis analyzer is being used, the cups may be slide to the testing position to get slow mixing and to avoid evaporation. Other techniques for mixing and for avoiding evaporation may be employed.

To assay, to each sample vessel 10 ul of an activator is added and immediately mixed, e.g., 3 times mixing with another pipet of 350 ul suspect HiT II patient whole blood. The sample vessel is then rapidly moved to the testing position and the test initiated. The test should be started within 30 seconds of adding the activator. The activator may be a combination of Reptilase® and FXIIIa or Reptilase®, FXIIIa and Epinephrine. Once the suspect HiT II patient whole blood and 10 ul of activator are added to each vessel, the first vessel will contain no added heparin, the second vessel will contain 1 U/ml heparin, the third vessel will contain 3 U/ml heparin and the fourth vessel will contain 30 U/ml heparin.

The test is continued until stable maximum amplitude is obtained. The expected positive result for HiT II is that either the second or third sample, 1 U/ml heparin or 3 U/ml heparin, respectively, will give an MA response greater than the sample 1 MA. For example, the MA of the second or third sample should be approximately 1.5-3 times greater than the MA for sample 1. In one embodiment the expected MA2 and/or MA3 is >10 mm, using the TEG® hemostasis analyzer parameter MA, and is 2 times greater than MA1 or MA4. This may be expressed as:

$$MA2 \text{ and/or } MA3\ 2X > MA1 \approx MA4$$

which is a positive indication for HiT II. The MA of sample 4, 30 U/ml heparin, should appear substantially equal to the MA of sample 1 due to the substantially complete platelet suppression of the overwhelming amount of heparin added to the sample. The patient whole blood testing protocol advantageously provides for point-of-care determination of HiT II.

Figure 5A:
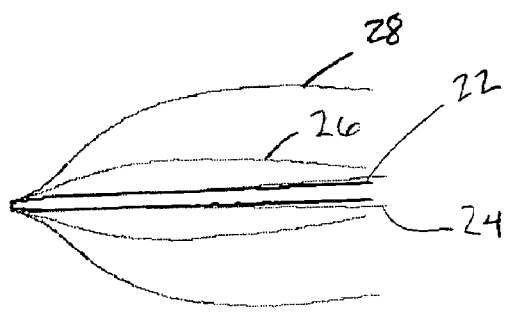
FIGS. 5a and 5b illustrates several hemostasis profiles taken in accordance with the protocol and apparatus of the embodiments of the invention.

A positive indication for HiT II is illustrated in FIG. 5a using results obtain from a TEG® hemostasis analyzer and referring to the parameter MA. Trace 22 represents MA1 and trace 24 represents MA4, both of which are substantially less than 10 mm, and on the order of 2-5 mm. Trace 26 represents MA2 and trace 28 represents MA3, both of which are substantially greater than 10 mm, and on the order of 15 mm and 40 mm, respectively. Thus, both MA2 and MA3 are greater than 10 mm and greater than 2 time either MA1 or MA4, which are substantially equal providing a positive indication for HiT II.

Figure 5B:
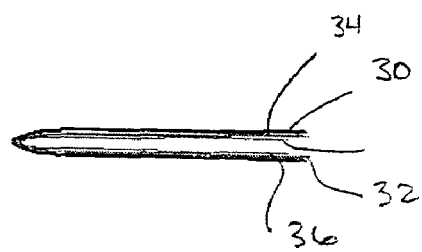

FIG. 5b illustrates the absence of HiT II. Trace 30 represents MA1 and trace 32 represents MA4, both of which are substantially less than 10 mm, and on the order of 2-5 mm. Trace 34 represents MA2 and trace 46 represents MA3, both of which are also less than 10 mm, and on the order of 2-5. Thus, both MA2 and MA3 are less than 10 mm and approximately equal to MA1 or MA4, providing a negative indication for HiT II.

An assay kit may be prepared. Such a kit may include a plurality of testing vessels, a quantity of heparin and a quantity of activator. Each of the testing vessels will be configured to hold a blood sample for testing in a blood hemostasis analyzer. For example, for the TEG® hemostasis analyzer, the testing vessel will be a cup 12, and four cups would be provided. For other types of testing apparatus, different vessels may be used. The quantity of heparin should be sufficient to prepare the required heparinized blood samples for testing. However, the kit may include three separate tubes/vials of heparin in the appropriate concentrations for the assay, as described above. A quantity of activator sufficient to activate the blood samples is also included in a separate tube/vial. The kit may also contain a quantity of PPACK in a tube/vial. The tubes/vials may be color coded, numbered or otherwise marked. The kit may be separable so as to facilitate storage. For example, PPACK may be provided in a 5 mg vial. The PPACK is then reconstituted with 1 ml saline, and the reconstituted PPACK should be stored at 0 to −4 degrees C., and will remain stable for several months. The required amount may be removed from the kit and the remainder returned to storage.

Unopened heparin stock, such as the above-described 1 U/ml, 3 U/ml and 30 U/ml heparin vials, may be stored at 0 to −4 degrees C. and will remain stable for several months. Opened tubes should be discarded within one week after opening.

Unopened vials of activator, which may contain approximately 1.8 ml, should be stored at −70 degrees C. and will remain stable for several weeks. Opened stock should be discarded within 8 hours of opening. Each vial may be sized, therefore, to provide only enough activator for each of the four samples. The activator should be thawed to room temperature before use.

Activator components may also be provided in stock vials from which activator is prepared to conduct assays. For example, a measure of activator, e.g., 180 µl, may be drawn into a tube from the provided stock vial. Depending on the assay type, additional components may-be added. For example, for the normal donor plus citrated patient plasma test, Example 1 above, 20 µl 2M $CaCl_2$ may be added along with 10 µl 1 mM Epinephrine. For the whole blood test, Example 2 above, 20 µl saline may be added along with 10 µl 1 mM Epinephrine. Other activators may be utilized depending on the availability of activator components and the type of test to be conducted.

The invention has been described in terms of several preferred embodiments and examples. One of skill in the art will appreciate that the invention may be otherwise embodied without departing from its fair scope, which is set forth in the subjoined claims.

We claim:

1. An apparatus for determining heparin-induced thrombocytopenia complex (HiT) comprising:
   a first hemostasis testing cell to test a first portion of a whole blood sample taken from a HiT suspect patient to determine a first blood sample characteristic including at least one of clot strength, clot elasticity, clot rate of formation and a clot rate of lysis of the first portion and to provide first blood sample characteristic data indicative of the same;
   a second hemostasis testing cell to test a second portion of the whole blood sample to determine a second blood sample characteristic including at least one of clot strength, clot elasticity, clot rate of formation and a clot rate of lysis of the second portion and to provide second blood sample characteristic data indicative of the same, the second portion having heparin added in vitro in a quantity sufficient to overwhelm platelet activation within the second portion; and
   a processor coupled to the first testing cell and the second testing cell to receive the first blood sample characteristic data and the second blood sample characteristic data, respectively, the processing being programmed to provide an indication of the presence of HiT based upon the first blood sample characteristic data and the second blood sample characteristic data.

2. The apparatus of claim 1, the quantity comprises a quantity of heparin in excess of or equal to 5 microliters (ul) of 1 Units/milliliter (U/ml).

3. The apparatus of claim 1, the quantity comprises a quantity of heparin in excess of or equal to 5 microliters (ul) of 3 Units/milliliter (U/ml).

4. The apparatus of claim 1, the quantity comprises a quantity of heparin in excess of or equal to 5 microliters (ul) of 30 Units/milliliter (U/ml).

5. The apparatus of claim 1, the quantity comprises a quantity of heparin in the range of 5 microliters (ul) of 1 Units/milliliter (U/ml) to 5 microliters (ul) of 30 Units/milliliter (U/ml).

6. The apparatus of claim 1, wherein the second blood sample characteristic represents a fibrin contribution to hemostasis.

7. The apparatus of claim 1, wherein the first blood sample characteristic represents a contribution to hemostasis of activated platelets in the presence of HiT.

8. The apparatus of claim 1, comprising a third hemostasis testing cell to test a third portion of the whole blood sample to determine a third blood sample characteristic including at least one of clot strength, clot elasticity, clot rate of formation and a clot rate of lysis of the third portion and to provide third blood sample characteristic data indicative of the same, the third portion having heparin added in vitro in another quantity, different than the quantity sufficient to overwhelm platelet activation within the second portion; and
   the processor being coupled to the third testing cell to receive the third blood sample characteristic data and the processor being programmed to provide an indication of the presence of HiT based upon the first blood sample characteristic data, the second blood sample characteristic data and the third blood sample characteristic data.

9. The apparatus of claim 1, wherein each of the first portion and the second portion comprises a platelet rich plasma (PRP)-patient plasma mixture.

10. The apparatus of claim 1, wherein each of the first portion and the second portion comprises patient whole blood.

11. The apparatus of claim 1, wherein each of the first portion and the second portion comprises an activator.

12. The apparatus of claim 1, wherein the first testing cell and the second testing cell each are testing cells of a multi-testing cell hemostasis testing machine.

13. The apparatus of claim 1, wherein the first testing cell comprises a testing cell of a first hemostasis testing machine and the second testing cell comprises a testing cell of a second hemostasis testing machine.

14. The apparatus of claim 11, wherein the activator comprises a compound effective to promote clot formation.

15. The apparatus of claim 11, wherein the activator comprises a compound effective to produce fibrin.

16. The apparatus of claim 11, wherein the activator comprises a compound effective to stabilize cross-linked fibrin.

17. The apparatus of claim 11, wherein the activator comprises a compound including Retilase and Factor XIIIa.

18. The apparatus of claim 1, wherein the first blood sample characteristic a first blood sample clot strength and the second blood sample characteristic comprises a second blood sample clot strength, and the processor is programmed to provide a comparison of the first blood sample clot strength and the second blood sample clot strength.

19. The apparatus of claim 18, wherein the processor is programmed to provide a comparison of at least two times the first blood sample clot strength relative to the second blood sample clot strength.

20. The apparatus of claim 8, wherein the first blood sample characteristic a first blood sample clot strength, the second blood sample characteristic comprises a second blood sample clot strength and the third blood sample characteristic comprises a third blood sample clot strength, and the processor is programmed to provide a comparison of the first blood sample clot strength, the second blood sample clot strength and the third blood sample.

21. The apparatus of claim 20, wherein the processor is programmed to provide a comparison of at least two times the first blood sample clot strength or the third blood sample clot strength relative to the second blood sample clot strength.

* * * * *